United States Patent
Dadachova et al.

(10) Patent No.: US 10,702,614 B2
(45) Date of Patent: Jul. 7, 2020

(54) RADIOBACTERIA FOR THERAPY OF CANCER

(75) Inventors: Ekaterina Dadachova, Mahopac, NY (US); Claudia Gravekamp, New York, NY (US); Arturo Casadevall, New York, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 0 days.

(21) Appl. No.: 13/985,087

(22) PCT Filed: Feb. 3, 2012

(86) PCT No.: PCT/US2012/023785
§ 371 (c)(1),
(2), (4) Date: Sep. 3, 2013

(87) PCT Pub. No.: WO2012/112317
PCT Pub. Date: Aug. 23, 2012

(65) Prior Publication Data
US 2014/0147379 A1 May 29, 2014

Related U.S. Application Data

(60) Provisional application No. 61/442,978, filed on Feb. 15, 2011.

(51) Int. Cl.
*A61K 51/12* (2006.01)

(52) U.S. Cl.
CPC ................................ *A61K 51/1203* (2013.01)

(58) Field of Classification Search
None
See application file for complete search history.

(56) References Cited

U.S. PATENT DOCUMENTS

| | | |
|---|---|---|
| 4,800,959 A | 1/1989 | Costerton et al. |
| 6,051,237 A | 4/2000 | Paterson |
| 6,562,316 B1 * | 5/2003 | Edwards ............... A61K 9/1271 424/1.21 |
| 6,565,852 B1 | 5/2003 | Paterson |
| 6,767,542 B2 | 7/2004 | Paterson et al. |
| 6,855,320 B2 | 2/2005 | Paterson |
| 7,135,188 B2 | 11/2006 | Paterson |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,700,344 B2 | 4/2010 | Paterson et al. |
| 7,794,729 B2 | 9/2010 | Paterson et al. |
| 7,820,180 B2 | 10/2010 | Singh et al. |
| 8,114,414 B2 | 2/2012 | Paterson et al. |
| 2005/0123440 A1 * | 6/2005 | Wien .................. C12Q 1/10 422/400 |
| 2005/0255043 A1 * | 11/2005 | Hnatowich et al. ......... 424/9.1 |
| 2006/0104955 A1 * | 5/2006 | Redshaw .................... 424/93.2 |
| 2008/0193373 A1 | 8/2008 | Stritzker et al. |
| 2009/0180955 A1 | 7/2009 | Stritzker et al. |
| 2009/0238757 A1 | 9/2009 | McBride et al. |
| 2009/0297542 A1 | 12/2009 | Masignani |

FOREIGN PATENT DOCUMENTS

| | | | |
|---|---|---|---|
| WO | WO 0125399 A2 | * | 4/2001 |
| WO | 2012112317 A1 | | 8/2012 |

OTHER PUBLICATIONS

Yu et al. Visualization of tumors and metastases in live animals with bacteria and vaccinia virus encoding light-emitting proteins. 2004 Nat. Biotechnol. 22: 313-320.*
Sundram et al. Preliminary results of transarterial rhenium-188 HDD lipiodol in the treatment of inoperable primary hepatocellular carcinoma. 2004 Eur. J. Nucl. Med. Mol. Imaging 31: 250-257.*
Ariel Im. Treatment of inoperable primary pancreatic and liver cancer by the intra-arterial administration of radioactive isotopes (Y90 radiating microspheres). 1965 Ann. Surg. 162: 267-278.*
Auvinen et al. A randomized trial of choice of treatment in prostate cancer: the effect of intervention on the treatment chosen. 2004 BJU Int. 93: 52-56. (Year: 2004).*
PCT International Search Report dated May 23, 2012 in connection with PCT International Patent Application No. PCT/US2012/23785, 5 pages.
PCT Written Opinion of the International Searching Authority dated May 23, 2012 in connection with PCT International Patent Application No. PCT/US2012/23785, 5 pages.
PCT Notification Concerning Transmittal of International Preliminary Report on Patentability and Written Opinion of the International Searching Authority dated Aug. 29, 2013 in connection with PCT International Patent Application No. PCT/US2012/023785, 7 pages.
Rauxe, R V, "Food Safety and Irradiation: Protecting the Public from Foodborne Infections" Emerg Infect Dis. Jun. 2001, http://dx.doi.org/10.3201/eid0707.017706.
Sheng W, et al., Feb. 2009;49(2):269-73. [Immunogenicity comparison of Listeria monocytogenes inactivated by gamma-irradiation or traditional treatments]. [Article in Chinese], (Abstract in English).
Oberstein P E et al., "Pancreatic cancer: why is it so hard to treat?" Therapeutic Advances in Gastroenterology. 2013; 6(4):321-337.
Tutt, B, OncoLog, Mar. 2014, vol. 59, No. 3, "Should the Primary Tumor Be Treated in Patients With Metastatic Prostate Cancer?" https://www2.mdanderson.org/depts/oncolog/articles/14/3-mar/3-14-3.html.
PCT International Search Report and Written Opinion, dated Mar. 16, 2016 in connection with PCT International Application No. PCT/US2015/56190, 8 pages.
Robson J et al., entitled "Observations on the Labelling of a Strain of *Staphylococcus aureus* with Phosphorus-32," J. gen. Microbiol., 1964, 36, 37-48.

* cited by examiner

*Primary Examiner* — Jennifer Lamberski
(74) *Attorney, Agent, or Firm* — Cantor Colburn LLP

(57) ABSTRACT

A method of treating a tumor in a subject, or reducing or preventing metastasis of a tumor in a subject, is provided comprising administering to the subject an amount of a bacteria labelled with, or comprising, one or more radionuclides so as to treat the tumor in the subject, or so as to reduce or prevent metastasis of the tumor in the subject. Radiobacteria-containing compositions and pharmaceutical compositions are also provided.

9 Claims, 9 Drawing Sheets

A

B

RADIOBACTERIA FOR THERAPY OF CANCER

CROSS-REFERENCE TO RELATED APPLICATIONS

This application is a U.S. national stage entry under 35 U.S.C. § 371 of PCT International Patent Application No. PCT/US2012/023785, filed Feb. 3, 2012, which claims benefit of U.S. Provisional Patent Application No. 61/442,978, filed Feb. 15, 2011, the contents each of which are incorporated herein by reference into the subject application.

STATEMENT OF GOVERNMENT SUPPORT

This invention was made with government support under grant numbers AG023096 and CA129470 awarded by the National Institutes of Health. The government has certain rights in the invention.

BACKGROUND OF THE INVENTION

Throughout this application various publications are referred to by number in parentheses. Full citations for these references may be found at the end of the specification. The disclosures of these publications and of all books, patents and patent application publications cited herein, are hereby incorporated by reference in their entirety into the subject application to more fully describe the art to which the subject invention pertains.

Pancreatic ductal adenocarcinoma, synonymous to pancreatic cancer, is the 4th leading cause of cancer deaths. The "silent killer" is characterized by its metastatic behavior (3) before the primary tumor can be detected, resulting in a five-year survival rate of only 4%. Current cancer treatments, i.e. surgery, followed by radiation and/or chemotherapy, are ineffective against metastases. Gemcitabine and erlotinib, FDA-approved drugs for pancreatic cancer treatment, improve median survival by approximately six months in advanced stage patients (1-3), emphasizing the need for new alternative therapies for pancreatic cancer. One such approach could be *Listeria monocytogenes*-based cancer therapy.

This laboratory discovered that a highly attenuated Listeria (Listeria$^{at}$) provides a therapeutic approach that is particularly useful against metastatic cancer. Myeloid derived suppressor cells (MDSC) are normally a major problem in cancer vaccination because they strongly suppress T cell and natural killer (NK) cell responses and promote angiogenesis (4-10), resulting in the development of metastases. However, when infected with Listeria$^{at}$ MDSC protect Listeria$^{at}$ from immune clearance through their immune suppressive character (Chandra et al., unpublished results), and deliver Listeria$^{at}$ safely to the tumor microenvironment where it infects and kills tumor cells through high levels of reactive oxygen species (ROS) (11). Also, Listeria$^{at}$-specific cytotoxic T lymphocytes (CTL) kills tumor cells, because infected tumor cells present Listeria$^{at}$ antigens (11). Importantly, in normal tissues that lack immune suppression Listeria$^{at}$ is rapidly cleared by macrophages, NK cells and CTL (11,12) which makes such treatment safe for human use.

Targeted radionuclide therapy has proven to be successful in treatment of several types of cancer and employs radiolabeled small molecules, monoclonal antibodies, peptides and other tumor-targeting vehicles (13). The radioactive particles emitted by the radionuclides physically destroy the cancerous cells and such therapies are not subject to multi-drug resistance mechanisms. There have been attempts to utilize targeted radionuclide therapy in the form of radiolabeled tumor specific antibodies (Ab) (radioimmunotherapy) for treatment of pancreatic cancer. However, radioimmunotherapy of pancreatic cancer has shown very modest results both pre-clinically (14-16) and in cancer patients with unresectable liver metastases (17). New choices of targeting vehicles are needed to make targeted radionuclide therapy successful in treatment of pancreatic cancer.

The present invention addresses the need for new targeted cancer therapies by providing "radiobacteria", including radiolisteria, to treat tumors, including inoperable tumors.

SUMMARY OF THE INVENTION

A method of treating a tumor in a subject, or reducing or preventing metastasis of a tumor in a subject, comprising administering to the subject an amount of a bacteria labelled with, or comprising, one or more radionuclides so as to treat the tumor in the subject, or so as to reduce or prevent metastasis of the tumor in the subject.

A composition comprising an amount of bacteria labelled with, or comprising, one or more radionuclides.

A pharmaceutical composition comprising an amount of bacteria labelled with, or comprising, one or more radionuclides and a pharmaceutically acceptable carrier.

Radionuclide-labelled bacteria, or bacteria comprising a radionuclide, for the treatment of a tumor or for preventing or reducing metastases of a tumor.

BRIEF DESCRIPTION OF THE DRAWINGS

In FIG. 3A the p value for comparisons of saline and RL, is 0.0003; for listeria and RL is 0.0007; for RL and $^{188}$Re is 0.0016; for saline and listeria is 0.0350; for listeria and $^{188}$Re is 0.1775; and for saline and $^{188}$Re is 0.4160. In FIG. 3B the p value for comparisons of saline and RL is 0.0030; for listeria and RL is 0.0368; for RL and $^{188}$Re is 0.0126: for saline and listeria is 0.0960; for listeria and $^{188}$Re is 0.5143: and for saline and $^{188}$Re is 0.4318.

In FIG. 4A the p value for comparisons of saline and RL is 0.0249; for listeria and RL is 0.0022; for RL and $^{188}$Re is 0.0651. In FIG. 4B the p value for comparisons of saline and RL is 0.0411; for listeria and RL is 0.0163 for RL and $^{188}$Re is 0.1320.

DETAILED DESCRIPTION OF THE INVENTION

Figure 1A:
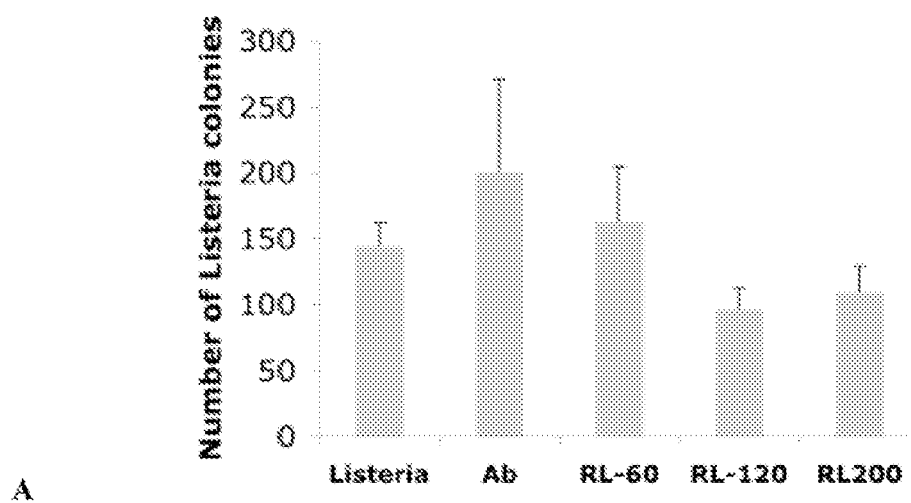
FIGS. 1A-1B: Effect of increasing doses of $^{188}$Re-labeled antibody directed to *Listeria* upon viability of *Listeria*. Attenuated *Listeria monocytogenes* (Listeria$^{at}$) bacteria were incubated with 60, 120, and 200 µCi of $^{188}$Re-Abs (designated as RL-60, RL-120, and RL-200 in the figure), plated on agar (LB only) and next day analyzed for the number of CFU of Listeria$^{at}$, in order to analyze whether $^{188}$Re kills Listeria$^{at}$ bacteria (A). To analyze the stability of RL, a similar experiment was performed on LB agar plates with chloroamphenicol (B). All experiments were performed in triplicates and repeated two times. The results were averaged and subjected to statistical analysis. Mann-Whitney p<0.05 is statistically significant. The error bars represent the standard error of the mean (SEM).

A method of treating a tumor in a subject, or reducing or preventing metastasis of a tumor in a subject, comprising administering to the subject an amount of a bacteria labelled with, or comprising, one or more radionuclides so as to treat the tumor in the subject, or so as to reduce or prevent metastasis of the tumor in the subject.

In an embodiment the bacteria is *Listeria monocytogenes*. In an embodiment the bacteria is *Salmonella thyphimurium. Vibrio cholera, Clostridium*, or *Bifidobacterium breve*. In an embodiment the bacteria are labelled with, or comprise, a beta radiation emitter. In an embodiment the bacteria are labelled with, or comprise, $^{188}$Re or $^{32}$P. In an embodiment the bacteria are labelled with a radionuclide, and are labelled by the radionuclide being bound to an antibody attached to the bacteria. In an embodiment the bacteria comprise the one or more radionuclides, and comprise the one or more radionuclides by means of having been cultured in a radionuclide-containing medium. In an embodiment the bacteria comprise more than one radionuclide. In an embodiment the bacteria labelled with, or comprising, one or more radionuclides, are administered systemically to the subject. In an embodiment the bacteria labelled with, or comprising, one or more radionuclides are administered locally to the tumor in the subject. In an embodiment the bacteria labelled with, or comprising, one or more radionuclides are injected into the tumor in the subject. In an embodiment the tumor is a pancreatic tumor. In an embodiment the tumor is a tumor of the ovary, uterus, neck, head, breast, prostate, liver, lung, kidney, neurones, glia, colon, testicle, or bladder or is a hepatocellular cancer. In an embodiment the tumor is an inoperable tumor. In an embodiment the amount of bacteria labelled with, or comprising, the one or more radionuclides provides a radiation dose of 1-500 mCi. In an embodiment the amount of bacteria labelled with, or comprising, the one or more radionuclides provides a radiation dose of 100-200 mCi.

In a preferred embodiment, the bacteria of the inventions described herein are attenuated. In a preferred embodiment, the bacteria of the inventions described herein are isolated or purified.

A composition comprising an amount of bacteria labelled with, or comprising, one or more radionuclides. In an embodiment the composition comprises a pharmaceutically acceptable carrier.

A pharmaceutical composition comprising an amount of bacteria labelled with, or comprising, one or more radionuclides and a pharmaceutically acceptable carrier.

In an embodiment of the composition or pharmaceutical composition the bacteria are labelled with, or comprise a beta radiation emitter. In an embodiment of the composition or pharmaceutical composition the bacteria are labelled with, or comprise, $^{188}$Re or $^{32}$P. In an embodiment of the composition or pharmaceutical composition the bacteria are labelled with the one or more radionuclides and are labelled by the radionuclide being bound to an antibody attached to the bacteria. In an embodiment of the composition or pharmaceutical composition the bacteria are *Listeria*. In an embodiment of the composition or pharmaceutical composition the bacteria are *Listeria monocytogenes*.

Radionuclide-labelled bacteria, or bacteria comprising a radionuclide, for the treatment of a tumor or for preventing or reducing metastases of a tumor. In an embodiment the bacteria are *Listeria monocytogenes*. In an embodiment the bacteria are labelled with, or comprise, $^{188}$Re or $^{32}$P.

In an embodiment the amount of bacteria labelled with, or comprising, the one or more radionuclides provides a radiation dose of 1-500 mCi. In an embodiment the amount of bacteria labelled with, or comprising, the one or more radionuclides provides a radiation dose of 100-200 mCi.

The invention is particularly useful for types of cancer for which there are practically no effective treatments, like pancreatic cancer (which is almost always detected in metastatic form), ovarian cancer, cancers for which surgery to remove the primary tumor is not an option because of tumor location (as is often the case in head and neck cancers), inoperable hepatocellular carcinoma, and for metastatic disease which is recurrent or refractory to the standard treatments (with non-limiting examples being lung and colon cancers as well as breast cancer).

As used herein, "treating" a tumor means that one or more symptoms of the disease, such as the tumor itself, metastasis thereof, vascularization of the tumor, or other parameters by which the disease is characterized, are reduced, ameliorated, prevented, placed in a state of remission, or maintained in a state of remission. "Treating" a tumor also means that one or more hallmarks of the tumor may be eliminated, reduced or prevented by the treatment. Non-limiting examples of such hallmarks include uncontrolled degradation of the basement membrane and proximal extracellular matrix, migration, division, and organization of the endothelial cells into new functioning capillaries, and the persistence of such functioning capillaries.

As used herein, reducing or preventing metastasis of a tumor means that any of the symptoms of the disease, such as the metastases, the extent of spread thereof, the vascularization of the metastases or other parameters by which the disease is characterized are reduced, ameliorated, prevented, placed in a state of remission, maintained in a state of remission, or eliminated.

As used herein, "radiobacteria" means bacteria which have been labelled with or comprise (i.e. contain) one or more radionuclide(s). As used herein "radiolisteria" means *Listeria*, preferably *Listeria monocytogenes*, which have been labelled with or comprise (i.e. contain) one or more radionuclide(s). The bacteria or *Listeria* can be labelled with the radionuclide(s) by, for example, being labeled therewith via a radiolabelled antibody. In a non-limiting example, the bacteria or the *Listeria* are labelled with a polyclonal antibody comprising a radionuclide. In a non-limiting example, the bacteria or the *Listeria* are labelled with a monoclonal antibody comprising a radionuclide. The bacteria or the *Listeria* can comprise the radionuclide(s) by, for example, being grown with the radionuclide(s). For example, *Listeria* can be grown in the presence of such radionuclides which *Listeria* can then incorporate. In a non-limiting example, *Listeria* are grown in a P-32-containing substrate, eliminating the need for a *Listeria*-specific antibody.

"Radionuclide" as used herein means a radioisotope of an element. The choice of the particular radioisotope which the bacteria, such as *Listeria* comprises, or with which the antibody which attaches to the bacteria, such as *Listeria* is labeled, will be determined by the type of tumor to be treated and its localization in the body. Two characteristics are important in the choice of a radioisotope—emission range in the tissue and half-life. In a preferred embodiment, the radioisotope is a beta emitter. Examples of beta emitters include 188-Rhenium (half-life 16.7 hours), 90-Yttrium (half-life 2.7 days), 32-Phosphorous (half-life 14.3 days), 47-Scandium (half-life 3.4 days), 67-Copper (half-life 62 hours), 64-Copper (half-life 13 hours), 77-Arsenic (half-life 38.8 hours), 89-Strontium (half-life 51 days), 105-Rhodium (half-life 35 hours), 109-Palladium (half-life 13 hours), 111-Silver (half-life 7.5 days), 131-iodine (half-life 8 days), 177-Lutetium (half-life 6.7 days), 153-Samarium (half-life 46.7 hours), 159-Gadolinium (half-life 18.6 hours), 186-Rhenium (half-life 3.7 days), 166-Holmium (half-life 26.8 hours), 166-Dysprosium (half-life 81.6 hours), 140-Lantanum (half-life 40.3 hours), 194-Irridium (half-life 19 hours), 198-Gold (half-life 2.7 days), and 199-Gold (half-life 3.1 days). In a preferred embodiment, the beta-emitting radioisotope is the high-energy β-emitter 188-Rhenium ($E_{max}$=2.12 MeV). $^{188}$Re has the additional advantage that it emits γ-rays which can be used for imaging, for example to assess progress of treatment and successful localization of the radiobacteria, such as radiolisteria. Longer-lived isotopes such as 90-Yttrium (half-life 2.7 days), 177-Lutetium (half-life 6.7 days) or 131-Iodine (half-life 8 days) may also be used. Positron emitters, such as 68-Gallium (half-life 68 minutes), 18-Fluorine (half-life 110 minutes), and 61-Copper (half-life 3.4 hours), could also be used to treat abscesses, as well as disseminated diseases. In addition, radioisotopes which are Auger electron emitters and/or conversion electron emitters could be used; however, such radioisotopes need to be coupled to an antibody type which is internalized by the Listeria. Examples of Auger electron emitters include 67-Gallium (half-life 78 hours), 111-Indium (half-life 2.8 days), 123-Iodine (half-life 13 hours), 125-iodine (half-life 60 days) and 201-Thallium (half life 3 days). Examples of conversion electron emitters include 117m-Tin (half-life 13.6 days). Examples of radioisotopes that emit both Auger electrons and conversion electrons include 195m-Mercury (half-life 41.6 hours) and 195m-Platinum (half-life 4 days).

Alpha emitters, which have a short emission range in comparison to beta emitters, may be preferable for treatment of tumors or cancers that are disseminated in the body or in the blood. Examples of alpha emitters include 213-Bismuth (half-life 46 minutes), 223-Radium (half-life 11.3 days), 224-Radium (half-life 3.7 days), 225-Radium (half-life 14.8 days), 225-Actinium (half-life 10 days), 212-Lead (half-life 10.6 hours), 212-Bismuth (half-life 60 minutes), 211-Astatin (half-life 7.2 hours), and 255-Fermium (half-life 20 hours). In a preferred embodiment, the alpha-emitting radioisotope is 213-Bismuth. $^{213}$Bi emits a high LET α-particle with E=5.9 MeV with a path length in tissue of 50-80 μm. Theoretically a cell can be killed with one or two α-particle hits. $^{213}$Bi is currently available in generator form, which allows transportation of this isotope from the source to clinical centers within the United States and abroad.

As used herein an antibody labeled with a radionuclide/radioisotope can be a polyclonal antibody, a monoclonal antibody, or a fragment of a polyclonal antibody, or a fragment of a monoclonal antibody, wherein the fragments retain their binding ability, such as a monovalent or divalent Fab.

In an embodiment the bacteria, such as *Listeria*, is radiolabelled with a plurality of radioisotopes, for example at least one radioisotope in the plurality of different radioisotopes is a long range emitter and at least one radioisotope is a short range emitter. Examples of long range emitters include beta emitters and positron emitters. Examples of short range emitters include alpha emitters, Auger electron emitters, and conversion electron emitters. Positron emitters can also be intermediate range emitters depending on the energy of the positrons. In a preferred embodiment, the long-range emitter is a beta emitter and the short range emitter is an alpha emitter. Preferably, the beta emitter is 188-Rhenium. Preferably, the alpha emitter is 213-Bismuth. Combinations of different radioisotopes can be used, which include an admixture of any of an alpha emitter, a beta emitter, a positron emitter, an Auger electron emitter, and a conversion electron emitter, with physical half-lives from 30 minutes to 100 days. Preferably, the plurality of different radioisotopes is more effective in treating the tumor than a single radioisotope within the plurality of different radioisotopes, where the radiation dose of the single radioisotope is the same as the combined radiation dose of the plurality of different radioisotopes.

The dose of the radioisotope can vary depending on the localization of the tumor, the severity of the tumor, the method of administration of radiobacteria, such as radiolisteria, (local or systemic) and the decay scheme of the radioisotope. In order to calculate the doses which can significantly decrease or eliminate tumor without radiotoxicity to vital organs, a diagnostic scan of the patient with the radiobacteria, such as radiolisteria, with diagnostic radioisotope or with the low activity therapeutic radioisotope can be performed prior to therapy, as is customary in nuclear medicine. The dosimetry calculations can be performed using the data from the diagnostic scan.

Fractionated doses of radiobacteria, such as radiolisteria, can be used, or single doses, though the former may be preferable against tumors by being less radiotoxic to normal organs. Depending on the status of a patient and the effectiveness of the first treatment, the treatment may consist of one dose or several subsequent fractionated doses.

In one embodiment, the subject is a human, and the dose of the radioisotope delivered by way of radiobacteria, such as radiolisteria, is between 1-500 mCi. In different embodiments, the dose of the radioisotope delivered by way of radiobacteria, such as radiolisteria, is between 1-100 mCi, 101-200 mCi, 201-300 mCi, 301-400 mCi, or 401-500 mCi.

The radiobacteria, such as radiolisteria, therapy delivered herein can be administered over a period of time to the subject alone, or with an adjuvant, or in combination with another anti-cancer agent. In an embodiment, the anti-cancer agent is a chemotherapeutic.

Radiobacteria, such as radiolisteria, can be administered in any fashion known in the art for anti-tumor therapies. Any acceptable route of administration of the active compounds described herein can be used. For example, oral, lingual, sublingual, buccal, parenteral, intrabuccal, intrathecal, intracerebroventricular, intraperitoneal, intra-tumor or nasal administration can be effected without undue experimentation by means well known in the art.

For administration parenterally, such as, for example, by intravenous, intramuscular, intrathecal or subcutaneous injection, administration can be accomplished by incorporating the radiobacteria, such as radiolisteria, or a composition comprising such of the present invention into a solution or suspension. Such solutions or suspensions may also include sterile diluents such as water for injection, saline solution, fixed oils, polyethylene glycols, glycerine, propylene glycol or other synthetic solvents and other media with the proviso that they are compatible with radiobacteria, such as radiolisteria, viability. Buffers such as acetates, citrates or phosphates and agents for the adjustment of tonicity such as sodium chloride or dextrose may also be added to the extent they are compatible with radiobacteria, such as radiolisteria, viability. In non-limiting examples, the parenteral preparation can be enclosed in ampules, disposable syringes or multiple dose vials.

The radiobacteria, such as radiolisteria, may be associated with a pharmaceutically-acceptable carrier which is compatible with radiobacteria viability, thereby comprising a pharmaceutical composition. The pharmaceutical composition may comprise the radiobacteria in the pharmaceutically acceptable carrier. Alternatively, the pharmaceutical composition may consist essentially of the radiobacteria in a pharmaceutically acceptable carrier. Yet alternatively, the pharmaceutical composition may consist of the radiobacteria in a pharmaceutically acceptable carrier. The pharmaceutically-acceptable carrier must be compatible with the radiobacteria, and not unduly deleterious to the subject. The choice of carriers will depend on the method of administration.

The subject can be a mammal. In different embodiments, the mammal is a mouse, a rat, a cat, a dog, a horse, a sheep, a cow, a steer, a bull, livestock, a primate, a monkey, or preferably a human.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Here it is demonstrated for the first time that Listeria$^{at}$ coupled with radionuclide $^{188}$Rhenium ($^{188}$Re)— the resulting radioactive Listeria (RL) was safe and highly effective against metastatic pancreatic cancer in the Panc-02 model.

Example 1

Initially whether making Listeria radioactive ("radiolisteria") would affect viability of the Listeria was tested. Such experimentation was necessary as only live Listeria can selectively infect the tumors and thus deliver radionuclide into the tumors. 188-Rhenium ($^{188}$Re) was chosen, a radionuclide which emits powerful beta radiation, for radiolabelling Listeria. Its long-range beta particles can penetrate deep enough into the tumors to kill cells via 'cross-fire' effect but, simultaneously, most Listeria will likely be spared as they will generally be missed by beta particles because of their small size. "Cross-fire" is responsible for the therapeutic efficacy of FDA approved radiolabelled antibodies Zevalin® and Bexxar® used for treatment of primary, refractory and recurrent non-Hodgkin lymphoma, and in experimental targeted radionuclide therapies.

Figure 1B:
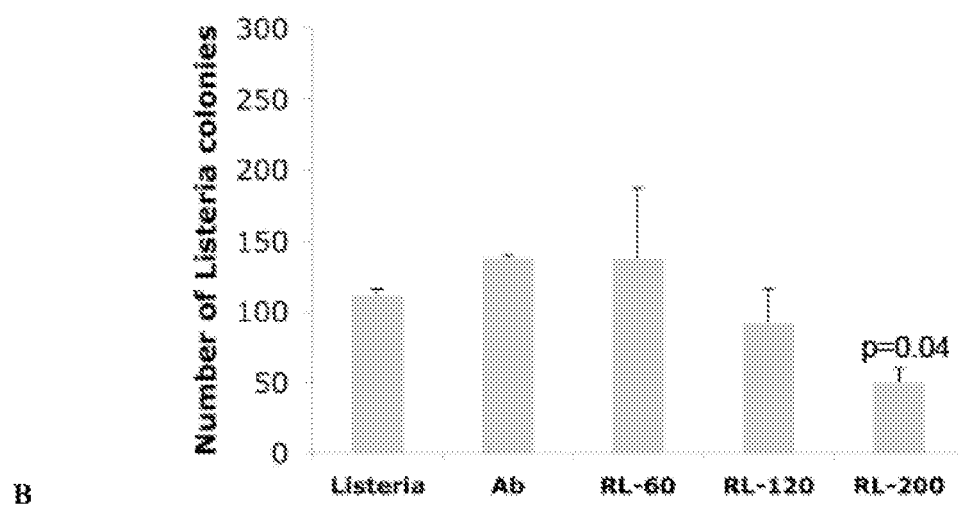

A commercially available polyclonal antibody to Listeria (BD Ditco Listeria O antiserum Poly serotype 1,4; Cat. #223021) was radiolabelled with $^{188}$Re (as in Dadachova E. et al. PNAS 2004, (5)) and 1×10$^8$ Listeria in 1 mL PBS were incubated either with 40 µg of unlabeled antibody, or with 60, 120 or 200 µCi of $^{188}$Re-antibody for 1 hr at 30° C., supernatant removed, and the $^{188}$Re-Listeria taken up in 1 mL PBS and plated with or without Chloroamphenicol. As seen from the viability data in FIG. 1, the increasing doses of radiolabelled antibody decreased to some extent Listeria's viability. However, even with the highest dose of 200 µCi at least 50% of Listeria remained viable. Thus, 200 µCi of $^{188}$Re-Listeria per injection was chosen in a follow-up therapy experiment.

Figure 2:
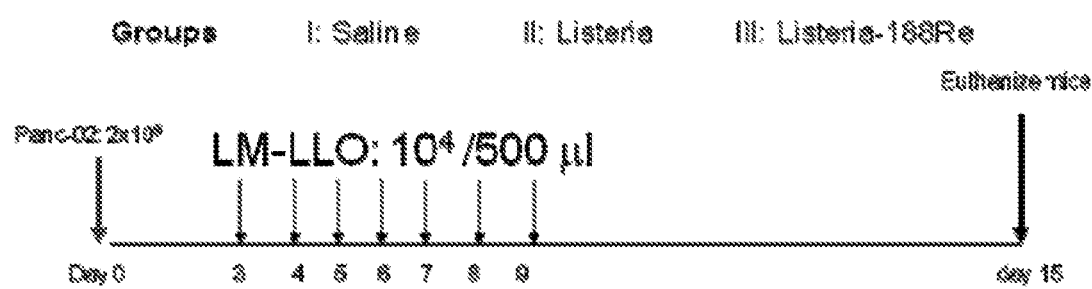
FIG. 2: Schematic of the testing of radiolabelled *Listeria* ("radiolisteria") efficacy in a pancreatic tumor model.
Figure 3A:
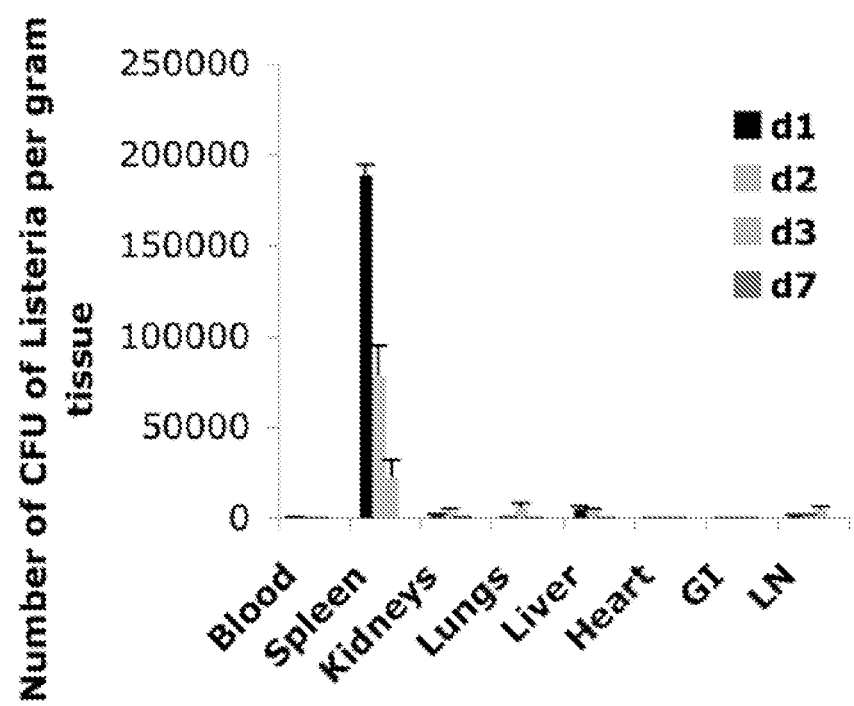
FIG. 3A-3E: A. Listeria$^{at}$ is cleared in all tissues. C57Bl6 mice without tumors were injected intraperitoneally (ip) once with a high dose of Listeria$^{at}$ (0.5×10$^7$ CFU), and analyzed for the presence of live Listeria$^{at}$ bacteria in all tissues 1, 2, 3, and 7 days later. n=3 mice. All experiments were performed in triplicate and the results were averaged. The error bars represent the standard error of the mean (SEM). n=5 mice per group. B. Therapeutic immunizations with RL strongly reduce the number of metastases in the Panc-02 model. Mice were therapeutically immunized eleven times with the low dose (10$^4$ CFU) of RL (Listeria$^{at}$-$^{188}$Re), Listeria$^{at}$, $^{188}$Re or Saline, and euthanized 21 days later. (B) Number of metastases and (C) tumor weight was determined. n=5 mice per group. This experiment was repeated three times, and the results were averaged. Mann-Whitney p<0.05=statistically significant. The error bars represent SEM. (D) From each group a representative is shown of metastases in the portal liver. (E) In the last of the three experiments $^{188}$Re was measured in all tissues of RL-treated mice one day after the last immunization by a gamma counter. The radioactive counts in each tissue were individually compared to the counts in the metastases using unpaired t test. p<0.05 is statistically significant. The error bars represent SEM.
Figure 3B:
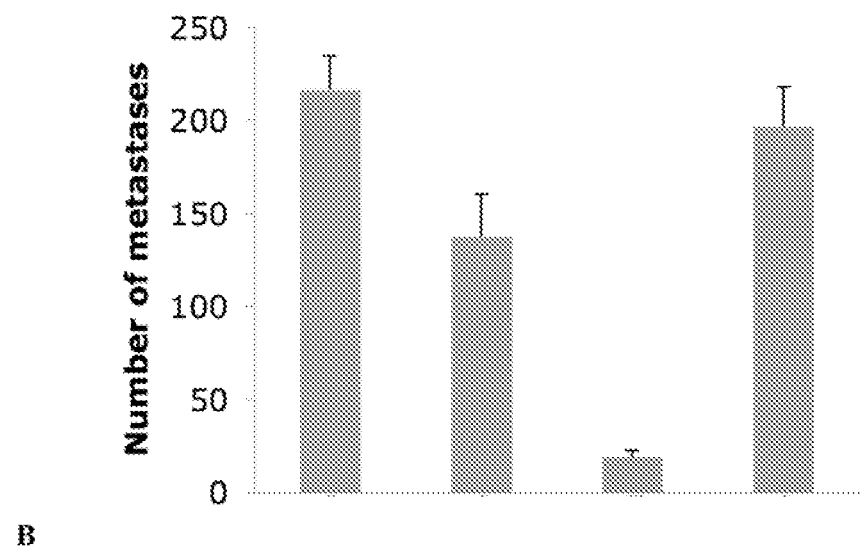
Figure 3C:
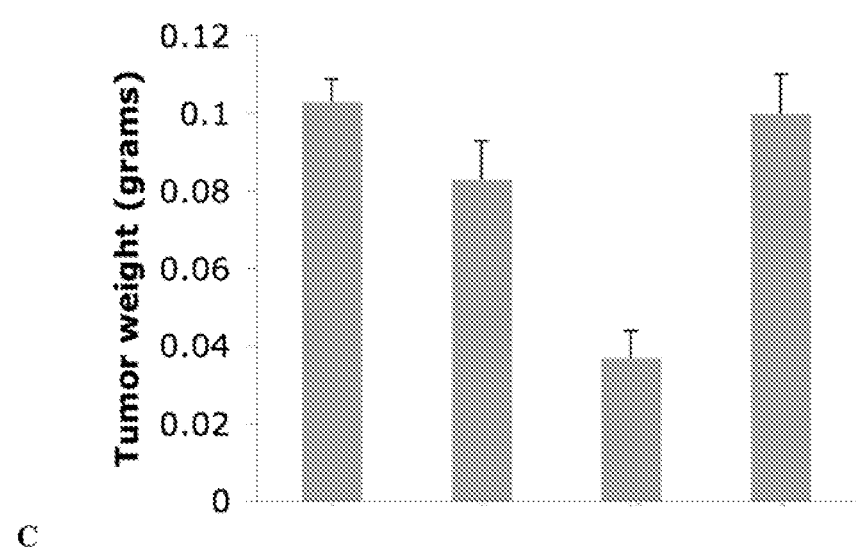
Figure 3D:
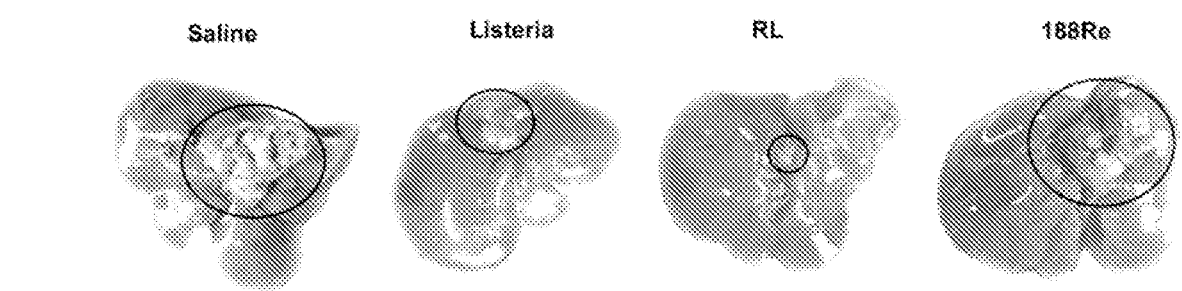
Figure 3E:
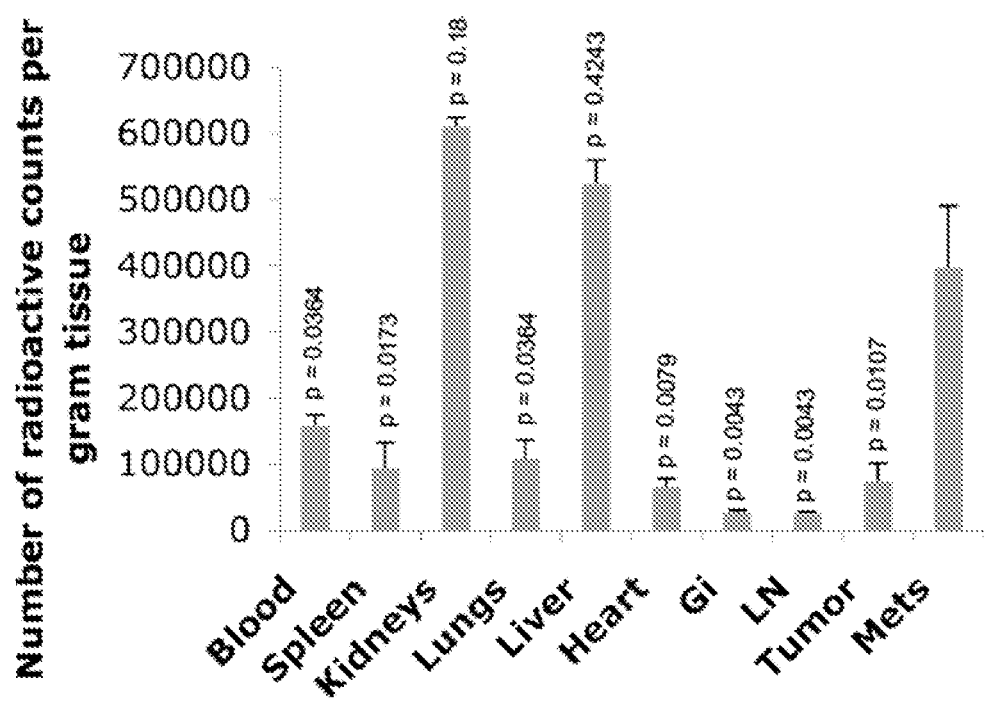

Next, in vivo tests were performed to determine the effectiveness of radiolisteria in a mouse model of metastatic pancreatic cancer: panc-02, an aggressive pancreatic mouse tumor model. C57BL6 mice were chosen for demonstration of the efficacy of radiolisteria. The schematic of the experiment is given in FIG. 2. There were 3 treatment groups— saline, Listeria alone and $^{188}$Re-Listeria (radiolisteria). Each mouse in each group received 7 daily intraperitoneal ("IP") injections of: 0.5 mL saline, or $^{188}$Re-Listeria cells in 0.5 mL saline, or 10$^4$ $^{188}$Re-listeria in 0.5 mL saline, respectively. The $^{188}$Re-Listeria were prepared in such a way that 1×10$^4$ Listeria cells were labeled with 200 µCi $^{188}$Re-antibody. Mice were sacrificed on Day 15 and their primary tumors and metastases were quantified.

Figure 4A:
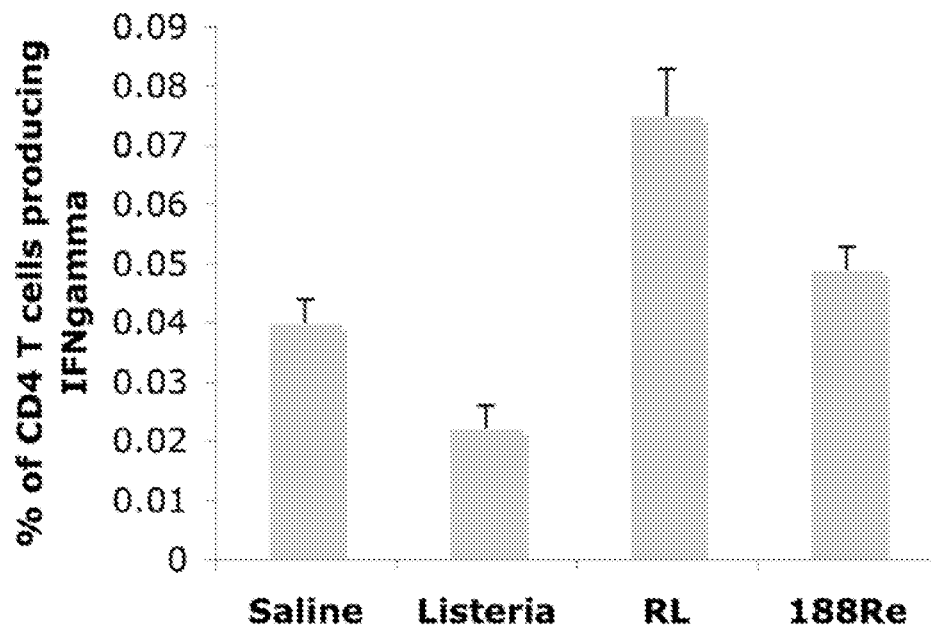
FIGS. 4A-4B: Therapeutic immunization with RL improves T cell responses in blood. Mice were therapeutically immunized eleven times with the low dose ($10^4$ CFU) of RL, Listeria. $^{188}$Re or Saline. CD4 (4A) and CD8 T cells (4B) producing IFNγ, were analyzed in the gated live lymphocyte population in blood by flow cytometry. n=5 mice per group. This experiment was performed twice. Mice were individually analyzed and the results were averaged. Mann-Whitney p<0.05=statistically significant. The error bars represent SEM.
Figure 4B:
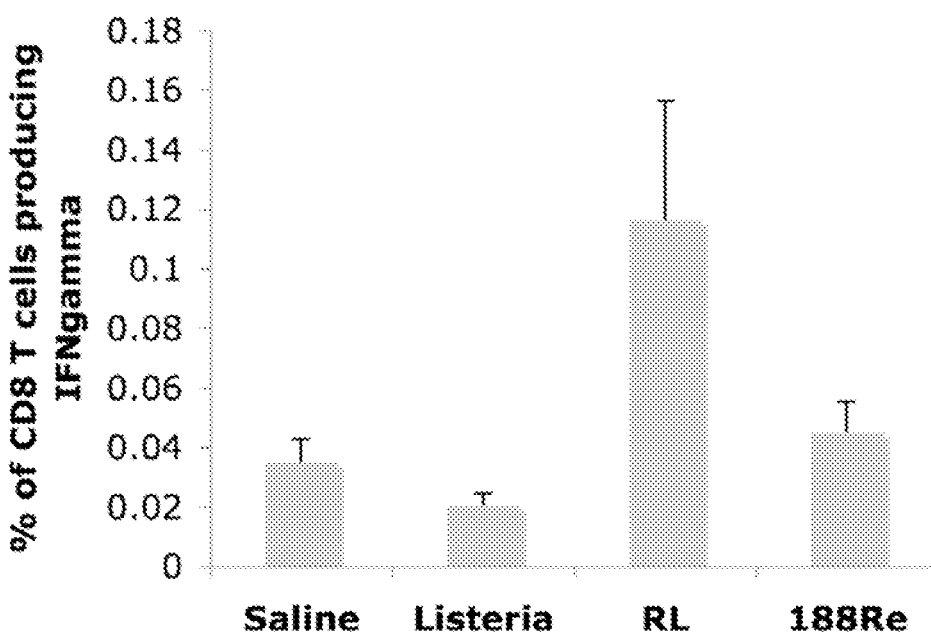
Figure 5:
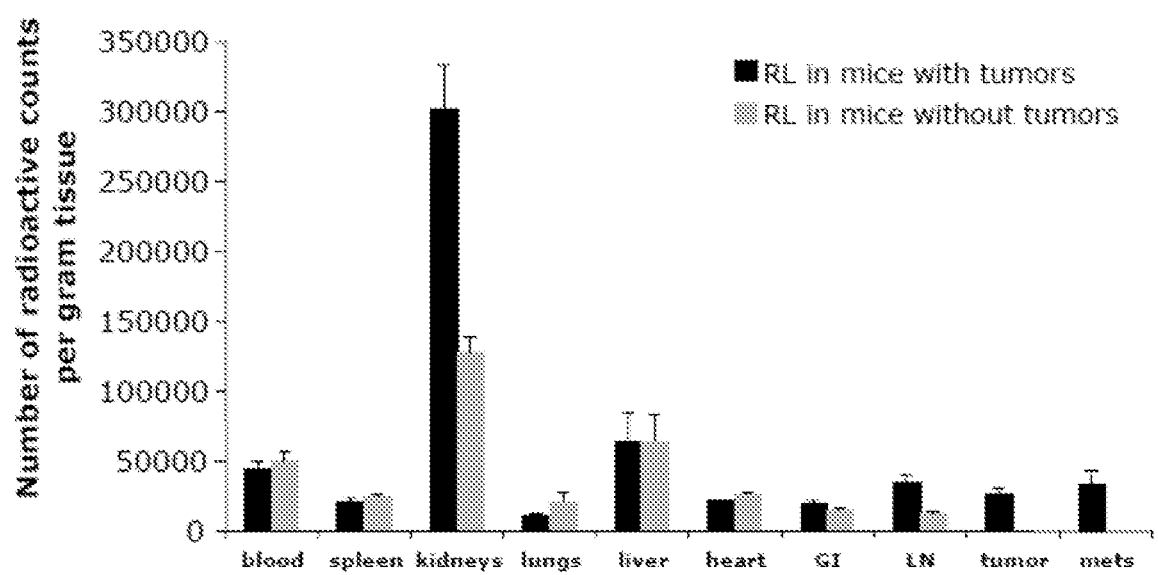
FIG. 5: Biodistribution of RL in mice with and without tumors. C57Bl6 mice with or without Panc-02 tumors were injected ip once with a high dose of RL ($0.5 \times 10^7$ CFU), and next day the various tissues were analyzed for radioactive counts by a gamma counter. The error bars represent SEM. n=5 mice per group.

Radiolisteria appeared to be highly effective against primary tumors (FIG. 3 upper panel) and especially against metastases (FIG. 3 lower panel and FIG. 4). In $^{188}$Re-Listeria-treated animals the number of metastases was reduced by 90% compared to the saline control group, and by 81% compared to the Listeria control group. Injections of $^{188}$Re-Listeria did not have any visible toxicity effect on the mice—they were active, maintained their feeding habits and did not lose weight throughout the duration of the experiment.

Coupling of Listeria$^{at}$ with $^{188}$Re does not kill or alter the stability of Listeria$^{at}$. $^{188}$Re has been successfully coupled to Listeria$^{at}$ using polyclonal antibodies (Abs) to Listeria$^{at}$ (18). The affinity and avidity of the Abs to Listeria is high and dissociation does not occur. Briefly, $10^3$-$10^8$ Listeria$^{at}$ bacteria in 1 mL PBS were incubated either with 1-40 µg of unlabeled Abs, or with 60, 120, and 200 µCi of $^{188}$Re-Abs for 0.5-3 hrs at 4 or 30° C. RL generated with the 60, 120, and 200 µCi of $^{188}$Re-Abs are designated here as RL-60, RL-120, and RL-200. Following the incubation, excess of $^{188}$Re-Abs was removed by centrifugation, and the various RLs were re-suspended in PBS and used for analysis.

An important question was whether $^{188}$Re kills the Listeria$^{at}$ bacteria. To analyze this question, serial dilutions of RL-60, RL120, and RL-200 as well as controls, i.e. Listeria$^{at}$ alone and Listeria$^{at}$ with unlabeled antibody were plated on agar and next day examined for the number of Listeria$^{at}$ colonies. Evidence that $^{188}$Re does not kill the Listeria$^{at}$ bacteria is shown in FIG. 1A, i.e. the number of Listeria$^{at}$ colonies counted in the RL groups was not significantly different from the numbers of colonies counted in the control groups. Another question was whether $^{188}$Re decreased the stability of the Listeria$^{at}$. The Listeria$^{at}$ strain used (XFL-7) contains a Listeria chloroamphemicol-resistant plasmid pGG34 while the *Listeria*$^{at}$ itself is chloroamphenicol sensitive. If the Listeria$^{at}$ is unstable and loses its pGG34 plasmid, it will not grow on chloroamphenicol. To analyze the stability of RL, serial dilutions of RL-60, RL-120, and RL200 as well as of Listeria$^{at}$ were plated on agar with chloroamphenicol. Somewhat lower (but significant) number of colonies was observed with RL-200 (which contained the highest concentration of $^{188}$Re-Ab (20 μCi)), compared to Listeria$^{at}$ alone when cultured with chloroamphenicol (FIG. 1B). In order to deliver sufficient amount of tumoricidal radiation to the tumors—we chose to use 200 μCi RL in all further experiments.

Efficacy of RL against metastatic pancreatic cancer in the Panc-02 model. In the original immunization protocol of Listeria$^{at}$, we immunized once a week with a high dose of Listeria$^{at}$ ($0.5\times10^7$ CFU) (19). However, as demonstrated here most of the Listeria$^{at}$ bacteria are cleared by day 3 and bacteria were completely cleared from all tissues by day 7 (FIG. 2). For therapeutic treatment, it is important to have a low level of live Listeria$^{at}$ that can continuously deliver the radioactivity into the tumors cells, without inducing Listeriosis. Therefore, a new immunization protocol was developed for the RL.

Mice were challenged with $2\times10^6$ Panc-02 tumor cells in the mammary fat pad on day 0. This resulted in a small primary tumor in the mammary fat pad palpable on 5-7 days, and metastases were found predominantly in the portal liver, accompanied with a strong production of ascites within 21 days. Three days after tumor cell injection, mice were immunized every day with $10^4$ CFU of RL/500 μl Saline (Group I). $10^4$ CFU of Listeria$^{at}$/500 μl Saline (Group II), 200 μCi $^{188}$Re/500 μl Saline (Group III), or 500 μl Saline (Group IV) on days 3-9, followed by a rest period of one week, followed by four immunizations with the same dose on days 16-19. All mice were euthanized on day 21 and analyzed for metastases and tumors. RL decreased the number of metastases by ~90% and Listeria$^{at}$ alone by ~50%, when compared to the Saline group or $^{188}$Re (FIG. 3A). An example of the metastases in the portal liver of each group is shown in FIG. 3B. The effect on primary tumors was less robust RL reduced the tumor weight by ~64% and the Listeria$^{at}$ by ~20% compared to the Saline group.

In the same experiment, we measured the amount of radioactivity that accumulated in metastases and normal tissues after the eleven immunizations. It was found that the radioactivity accumulated selectively in the metastases and much less in the primary tumors and normal organs, i.e. the radioactivity in the metastases was 4-15-fold higher compared to all other organs, except liver and kidneys (FIG. 3C). The radioactivity levels found in liver and kidneys were comparable to the metastases. One day after the last immunization the number of live Listeria$^{at}$ was also analyzed in all tissues, including metastases and tumors. It appeared that all tissues were negative for live Listeria$^{at}$ bacteria (data not shown). These results demonstrate that the low dose of Listeria$^{at}$ is more rapidly cleared than the radioactivity.

The effect of RL on T cell responses. In previous studies, this laboratory showed that Listeria$^{at}$ improved T cell responses (increased production of IFNγ) in mice with metastatic breast cancer after one preventive followed by two therapeutic immunizations with high dose Listeria$^{at}$ ($0.5\times10^7$ CFU: $LD_{50}=10^8$ CFU), once a week (11). In the current study, it was analyzed whether T cell responses also could be improved after eleven therapeutic immunizations with the low dose of RL ($10^4$ CFU). It was found that RL significantly enhanced the percentage of CD8 T cells producing IFNγ in blood compared to the Saline group, while the effect on CD4 T cell responses was less vigorous, but still significant (FIG. 4).

In the primary tumors, CD4 and CD8 T cell responses increased, but this was not significant (data not shown). Safety aspects of RL in mice with and without tumors Although both Listeria$^{at}$ and 188Re have mild side effects in human clinical trials in cancer patients (20-22), the combination of RL has never been tested for its safety in vivo. Therefore, various experiments were performed aimed at testing RL safety such as biodistribution of RL, $^{188}$Re, and Listeria$^{at}$, pathology and liver functions. First, the biodistribution of RL was measured in all tissues of tumor- and nontumor-bearing mice one day after one ip administration of a high dose of RL or Listeria$^{at}$ ($0.5\times10^7$ CFU), or with a comparable dose of $^{188}$Re. Next day all tissues were collected and measured for gamma radiation, and the number of live Listeria was determined. At the time of injection all mice had both a primary tumor and metastases, as well as ascites in the peritoneal cavity.

In mice with tumors that were immunized with RL, radioactivity was measured in all organs, including metastases and tumors (FIG. 5). However, kidneys and liver contained much higher levels of radioactivity than the organs or tumors and metastases (FIG. 5). A similar pattern was observed in mice without tumors but lower levels of radioactivity were measured. Free $^{188}$Re was not detectable in all tissues of mice with or without tumors and therefore not shown. Important for patient's safety, one week after the injection of the high dose RL, radioactivity was not measurable anymore in any of the tissues because of the short half-life time of $^{188}$Re, i.e. seventeen hrs (data not shown). The Listeria$^{at}$ pattern is different from the RL. As shown in FIG. 2A, next day after one immunization with the high dose of Listeria$^{at}$ (0.5×10$^7$ CFU), live Listeria$^{at}$ were mostly cultured from the spleen and not from liver or kidney. However, one week after injection live Listeria$^{at}$ bacteria were not detected in these tissues (FIG. 2A). Most importantly, one week after the eleven immunizations with the low dose of RL or Listeria$^{at}$ in the vaccine studies, radioactivity and live Listeria$^{at}$ could not be detected anymore (data not shown). Moreover, as mentioned earlier live Listeria$^{at}$ could not be detected anymore, already one day after the last of the eleven immunizations with low dose Listeria$^{at}$.

In addition, all tissues were analyzed for pathological damage by histopathology and serum was analyzed for liver functions such as aspartate transaminase (AST) and alanine transaminase (ALT), one week after the last of eleven immunizations with RL, Listeria$^{at}$, free $^{188}$Re, or Saline. No pathological damage was observed by RL, $^{188}$Re or Listeria$^{at}$ (Table 1), and liver functions were not altered by RL, $^{188}$Re, or Listeria (Table 2).

Figures 6A, 6B, 6C:
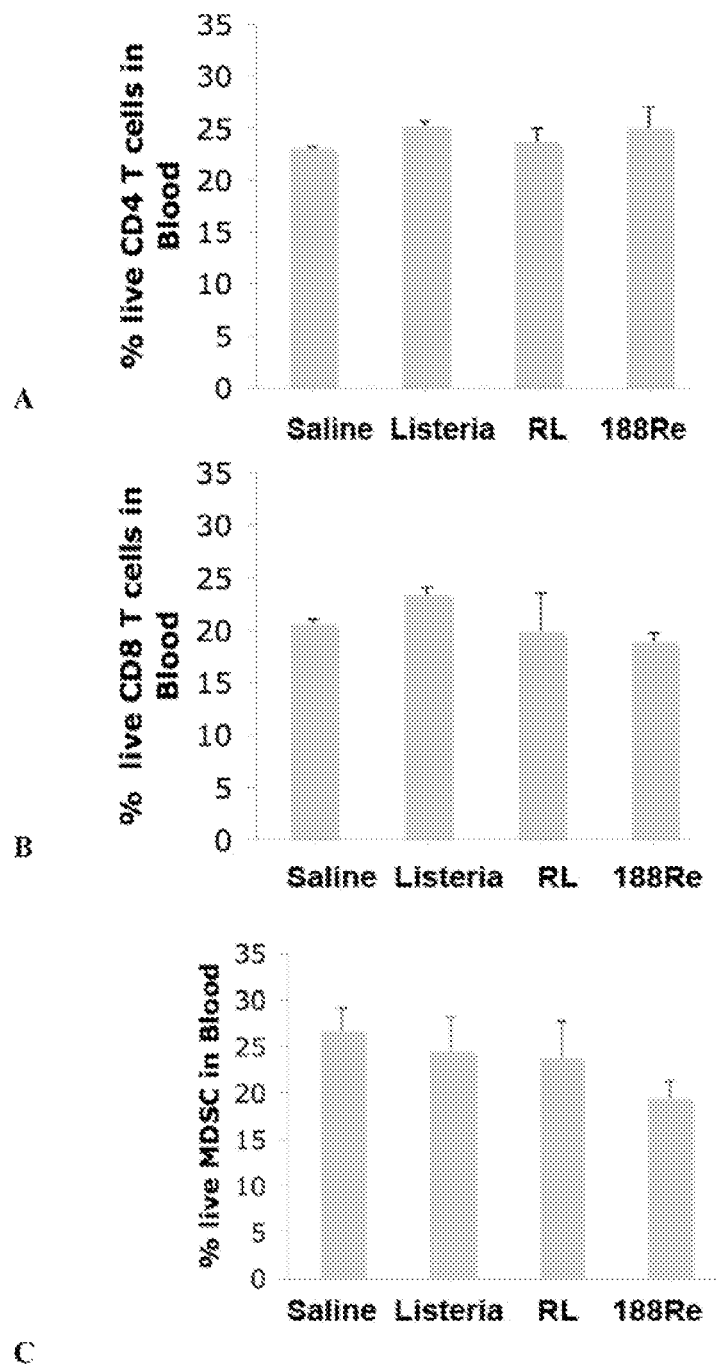
FIGS. 6A-6C: RL does not destroy T cells or MDSC. Mice were therapeutically immunized eleven times with the low dose ($10^4$ CFU) of RL, Listeria$^{at}$, $^{188}$Re or Saline. Two days after last immunization, mice were euthanized and analyzed for live CD4 and CD8 T cells as well as for live MDSC in blood by flow cytometry. The percentage of live CD4 and CD8 T cells was determined in the gated total live lymphocyte population of blood. The percentage of live MDSC(CD11b+Gr1+) was determined in the gated total live leukocyte population in blood. n=5 mice per group. This experiment was performed twice. Mice were individually analyzed and the results were averaged. All groups were compared to the Saline group. Mann-Whitney p<0.05 is statistically significant. The error bars represent SEM.
Figures 7A, 7B, 7C:
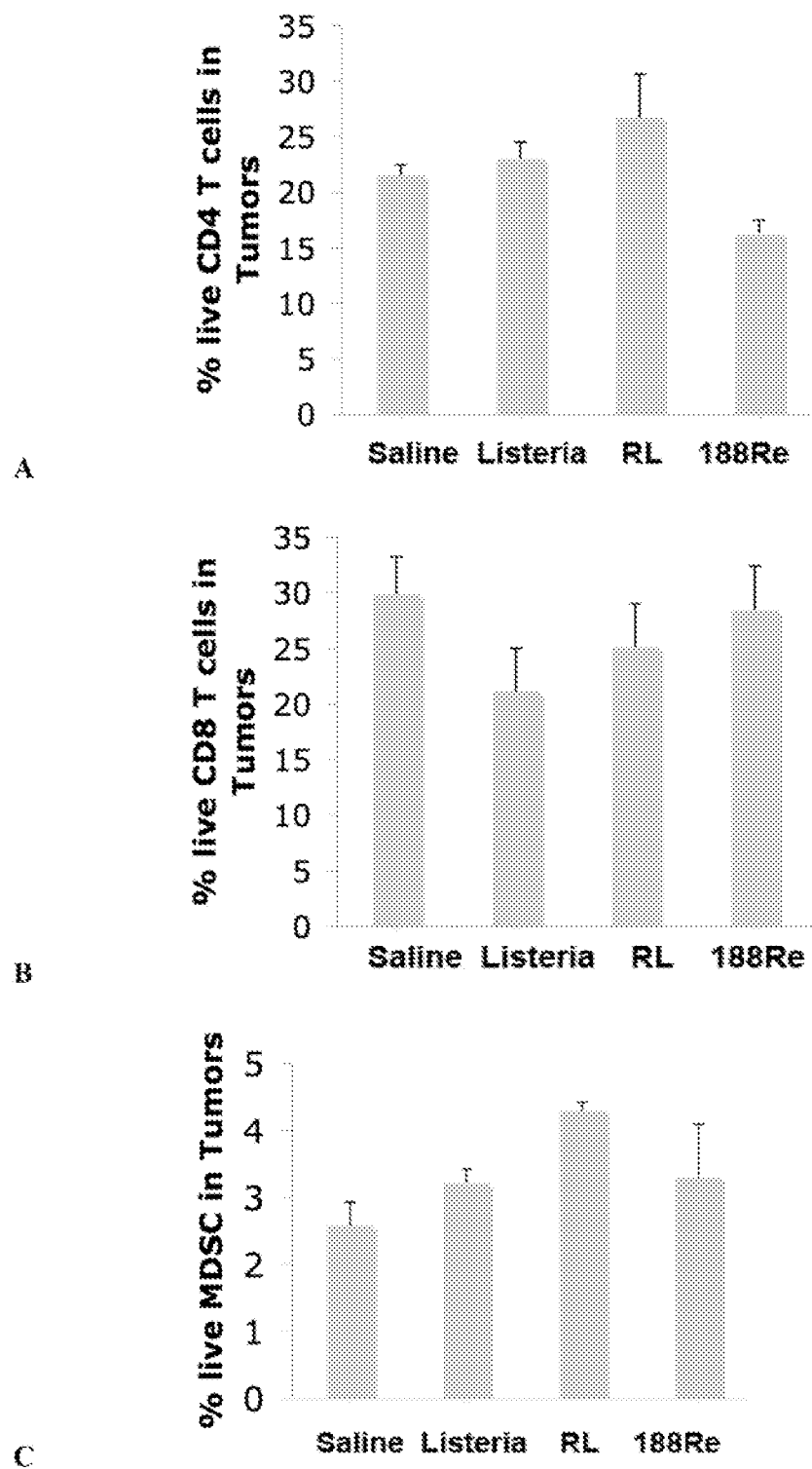
FIGS. 7A-7C: The mice described in FIGS. 6A-6C were also analyzed for live MDSC in primary tumors by flow cytometry. The percentage of live CD4 and CD8 T cells was determined in the gated total live population of tumors. The percentage of live MDSC (CD11b+Gr1+) was determined in the gated total live tumor cell suspension, including all immune cells, of the primary tumors. n=5 mice per group. This experiment was performed twice. Mice were individually analyzed and the results were averaged. All groups were compared to the Saline group. Mann-Whitney p<0.05= statistically significant. The error bars represent SEM.

Finally, it was analyzed whether RL destroyed T cells or MDSC. For this purpose, the effect of RL on viability of T cells and MDSC in blood and tumors was measured. No significant decrease was observed in the percentage of CD4 and CD8 T cells of the RL group compared to the Saline group (FIG. 6). No negative effect of RL was observed on MDSC (FIG. 6). In contrast, the percentage of MDSC increased slightly (but significantly) in the RL group compared to the Saline group in tumors but not in blood (FIG. 6).

In a previous study, this laboratory and others showed that Listeria$^{at}$ selectively targeted metastases in vivo (11.23). Also, bacteria have been genetically engineered for selectively delivery of anti-cancer agents into tumor cells in vivo (24). In the study presented here, evidence is provided that Listeria$^{at}$ delivers cytotoxic $^{188}$Re into the metastases of a highly aggressive pancreatic cancer model Panc-02. This addition of radiation resulted in a dramatic reduction in the number of metastases, compared to the Listeria$^{at}$ or Saline control groups, and efficacy correlated with accumulation of ionizing radiation of $^{188}$Re in the metastases. T cell responses were also analyzed since infected tumor cells present Listeria antigens, and becomes a highly sensitive target for Listeria-specific CTL (11). In addition, we have shown that Listeria kills tumor cells directly through high levels of ROS (11), and that this leads to activation of CTL against tumor-associated antigens (TAA) through cross presentation of TAA by dead tumor cells (Chandra et al., unpublished results). In the current study, we found that therapeutic treatment with RL significantly improved T cell responses compared to the control groups in blood of tumor-bearing mice. Also tumor cells killed by ionizing radiation of $^{188}$Re may activate T cells through cross presentation of TAA expressed by the dead Panc-02 cells, a phenomenon shown by others as well (25,26).

The dramatic effect of RL on the metastases in the Panc-02 model was repeatedly found without inducing severe side effects on normal tissues. Biodistribution experiments showed that Listeria$^{at}$ as well as radioactivity initially was detected in all tissues, including metastases and primary tumors as well as blood, one day after administration of a single high dose of Listeria$^{at}$ or RL (0.5×10$^7$ CFU). The highest burden of live Listeria$^{at}$ bacteria was found in the spleen. It was reported that the spleen was more susceptible to wild type Listeria in the early phase of infection than the other organs (27). One week after the injection, all Listeria$^{at}$ bacteria were rapidly cleared by the immune system in all tissues. One may expect that the highest number of radioactive counts should also be observed in the spleen. However, the highest levels of radioactivity were found in the kidneys and in liver. This is because $^{188}$Re and Abs from all tissues and blood will accumulate in the kidneys and liver for clearance through excretion and detoxification, respectively. Moreover, one week after the injection radioactivity could not be detected anymore because of the short half-life time of $^{188}$Re (seventeen hrs). Also examined was the biodistribution of $^{188}$Re and Listeria$^{at}$ after the eleven immunizations with the low dose of RL or Listeria$^{at}$ (10$^4$ CFU) in mice with or without tumors. It appeared that neither Listeria$^{at}$ (10$^4$ CFU) nor radioactivity was detected one week after the last immunization. Pathological examination revealed practically no side effects in normal tissues, and liver functions such as AST and ALT appeared to be unaltered, and no significant decrease was found in the percentage of CD4 and CD8 T cells in blood and primary tumors of the RL group compared to the Saline group. Interestingly, the percentage of MDSC in the RL group slightly (but significantly) increased compared to the Saline group in the primary tumors (but not in blood). Since RL accumulates after eleven immunizations in the tumors it may release more MDSC from the bone marrow, and then migrate to the tumor site. The Listeria$^{at}$ in this study is different from wild type Listeria.

Wild type Listeria does multiply in hepatocytes of the liver or in endothelial cells of the gastrointestinal tract (28.29), but attenuated Listeria$^{at}$ does not multiply in normal tissues because it is highly attenuated and rapidly cleared by the immune system. In conclusion, the results strongly suggest that RL is safe for human application. This laboratory and others have already shown that Listeria$^{at}$ or $^{188}$Re is less toxic in humans than chemotherapy (20-22). A remaining question is why RL, when accumulated in metastases and tumors as well as in normal kidneys and liver, destroys tumor cells, but not cells in normal kidney and liver. Radiation-induced irreparable DNA damage is much higher in proliferating cells, like metastases and tumors, than in non-dividing normal tissues. Also, Listeria$^{at}$ is faster cleared in normal than in tumor tissues (11), and therefore the ROS-induced damage in normal may be less than in tumor tissues (metastases an primary tumors). In contrast to tumor tissues, normal tissues do not express TAA and are therefore not a target for TAA-specific CTL.

In summary, Listeria$^{at}$ is particularly useful to battle metastatic cancer because it selectively delivers $^{188}$Re into metastases, without harming normal cells in vivo. Therefore, RL is highly pertinent for application in patients with pancreatic, kidney and liver cancers, as well as other cancers as well.

Materials and Methods

Mice: Normal female C57Bl/6 mice aged 3 months were obtained from Charles River and maintained in the animal husbandry facility Albert Einstein College of Medicine according to the Association and Accreditation of Laboratory Animal Care (AACAC) guidelines. All mice were kept under Bsl-2 condition as required for Listeria$^{at}$ vaccinations.

Cells and cell culture: The Panc-02 cell line was kindly provided by Chandan Guha (Department of Radiation Oncology, Albert Einstein College of Medicine, Bronx, N.Y.). The Panc-02 cells were cultured in McCoy's medium supplemented with 10% FBS, Glutamine (2 mM), nonessential amino acids, sodium pyruvate (1 mM), Hepes (10 mM), and Pen/Strep (100 U/ml).

Listeria$^{at}$-based vaccine: In this study, a highly attenuated *Listeria monocytogenes* (Listeria$^{at}$) was used as the vaccine, as described previously (19). The Listeria$^{at}$ plasmid pGG-34 is chloroamphenicol-sensitive, and expresses the positive regulatory factor A (prfA) as well as Listeriolysin O (LLO), required to escape the vacuole after infection (28). The coding region for the C-terminal part of the LLO (cytolytic domain that binds cholesterol in the membranes) protein in the plasmid has been deleted, but Listeria$^{at}$ is still able to escape the vacuole upon infection (30). Mutations have been introduced into the prfA gene and the remaining LLO (expressed by the pGG34 vector), which reduced the pathogenicity of the Listeria$^{at}$ (30). The Listeria$^{at}$ background strain used herein, XFL-7, lacks the prFA gene, and retains the plasmid in vitro and in vivo (31).

$^{188}$Rhenium and anti-Listeria antibodies: $^{188}$Re was obtained from $^{188}$W/$^{188}$Re radionuclide generator (Oak Ridge National Laboratory, TN). The commercially available polyclonal antibody to Listeria (IgG1 isotype, BD Difco Listeria O antiserum Poly serotype 1,4; Cat. #223021; This anti-serum has high avidity and affinity for Listeria$^{at}$ bacteria and does not dissociate (worldwideweb.bd.com/ds/productCenter/223021.asp)), and the isotype matching control Ab to account for any possible non-specific binding of the IgG to the Listeria$^{at}$ has been radiolabeled with $^{188}$Re as described previously (18).

Tumor challenge and immunizations: Tumor challenge and vaccinations were performed as described previously with minor modifications (11). Briefly, Panc-02 tumor cells ($2 \times 10^6$) were injected into the mammary fat pad on day 0. In the Panc-02 model, the primary tumor extends to the chest cavity lining which is palpable 5-7 days after tumor cell injection, but primary tumors stayed relatively small, while metastases predominantly develop in the portal liver, resulting in the production of ascites in the peritoneal cavity within approximately 20 days.

Metastases develop less frequently in the mesenteric lymph nodes (MLN), diaphragm, spleen and kidneys. Three days after tumor cell injection, mice were immunized every day (days 3-9) ip with a low dose of Listeriaat ($10^4$ CFU per 500 µl saline) ($LD_{50}=10^8$), 200 µCi RL (104 CFU per 500 µl saline), 2 µCi 188Re (the same dose of $^{188}$Re compared to Listeria-$^{188}$Re), or saline on days 3-9, followed by a rest period of one week, and then followed by four more immunizations on days 16-19 with $10^4$ CFU of Listeria$^{at}$, RL, $^{188}$Re, or Saline. All mice were euthanized at day 21, and analyzed for tumor weight, frequency and location of metastases as well as for T cell responses in blood and primary tumors.

Flow cytometry analysis: Immune cells from blood and primary tumors from individual mice were isolated as described previously (32,33). Briefly, red blood cells were lysed according to standard protocols, and the remaining leukocyte population was used for analysis. Single cell suspensions were obtained from primary tumors using GentleMacs combined with a mild treatment of the cells using Collagenase, Dispase, and DNAse I, according the manufacturers instructions (Miltenyi Biotec Inc, Auburn, Calif.).

Cells were first incubated with an Fc blocker (anti-CD16), and subsequently with the antibodies for the identification of different cell types. To identify CD4 and CD8 T cells, anti-CD8 antibodies were used. To detect the production of intracellular lymphokines the cytofix/cytoperm kit from Pharmingen according manufacturers instructions, and antibodies to IFNγ were used. To identify MDSC, anti-CD11b and anti-Gr1 antibodies were used. Appropriate isotype controls were used for each sample.

Depending on the sample size, 10,000-500,000 cells were acquired by scanning using a Fluorescence Activated Cell Sorter (flow cytometry)(BD-FACS-Calibur. Beckton and Dickinson, Franklin Lakes, N.J.), and analyzed using Flojo software, as described previously (33).

Isolation of Listeria from metastases, tumors and normal tissue: Mice with Panc-02 metastases and tumors were immunized once with a high dose Listeria$^{at}$ ($0.5 \times 10^7$ CFU), or eleven times with a low dose ($10^4$ CFU) and euthanized at various time points as indicated in the text. Metastases, tumors and normal tissues were dissected and homogenized, plated on agar, and counted for Listeria$^{at}$ colonies the next day. The number of Listeria$^{at}$ CFU was calculated per gram tissue.

Determination of radioactive counts in tumor and normal tissues: Mice with or without Panc-02 metastases and tumors were immunized once with a high dose Listeria$^{at}$ ($0.5 \times 10^7$ CFU), or eleven times with a low dose ($10^4$ CFU) and euthanized at various time points as indicated in the text. Metastases, tumors and normal tissues of RL-vaccinated and control mice were dissected, weighted, and analyzed for gamma radiation by a gamma counter (Wallac, Turku, Finland). The number of radioactive counts was calculated per gram tissue.

Statistical Analysis

To statistically analyze the effects of RL or Listeria$^{at}$ on the growth of metastases and tumors, on immune responses, or on liver functions in the pancreatic mouse tumor model, unpaired t test, Mann-Whitney test, or ANOVA were used. Values $p<0.05$ were considered statistically significant.

REFERENCES

1. A. Maitra, and R. H. Hruban, "Pancreatic cancer." *Annu. Rev. Pathol.* 3, 157-188 (2008).
2. M. J. Moore, D. Goldstein, J. Hamm. A. Figer, J. R. Hecht, S. Gallinger, H J. Au et al, Erlotinib plus gemcitabine compared with gemcitabine alone in patients with advanced pancreatic cancer: A Phase III trial of the National Cancer Institute of Canada Clinical Trials Group. *J Clin Oncol* 15, 1960-1966 (2007).
3. M. H. Kulke, L. S. Blaszkowski, D. P. Ryan, J. W. Clark, et al, Capecitabine plus Erlotinib in Gemcitabine-refractory advanced pancreatic cancer. *J. Clin. Oncol.* 25, 4787-4792 (2007).
4. D. I. Gabrilovich, and S. Nagaraj, Myeloid-derived suppressor cells as regulators of the immune system. *Nat. Rev. Immunol.* 9, 162-174 (2009).
5. S. Ostrand-Rosenberg, and P. Sinha, Myeloid-derived suppressor cells: Linking inflammation and Cancer. *J. Immunol.* 182, 4499-4506 (2009).
6. P. Serafini, and V. Bronte. Myeloid-derived suppressor cells in cancer. In: Tumor induced Immune Suppression. Eds Gabrilovich DI and Hurwitz AA. Springer. pp 157-194 (2008).
7. A. Mantovani, A. Sica, and M. Locati M. New vistas and macrophage differentiation and activation. *Eur. J. Immunol.* 37, 14-16 (2007).
8. P. Sinha, V. K. Clements, and S. Ostrand-Rosenberg, Interleukin-13-regulated M2 macrophages in combination with myeloid suppressor cells block immune surveillance against metastases. *Cancer Res.* 65, 11743-11751 (2005).
9. C. Murdoch, M. Muthana, S. B. Coffelt, and C. E. Lewis, The role of myeloid cells in the promotion of tumor angiogenesis. *Nature Reviews Cancer* 8, 618-631 (2008).

10. M. C. Schmid, and J. A. Varner, Myeloid cells in the tumor microenvironment: Modulation of tumor angiogenesis and tumor inflammation. *J. Oncol.* doi: 10.1155/2010/201026 (2010).
11. S. H. Kim, F. Castro, Y. Paterson, C. Gravekamp, High efficacy of a Listeria-based vaccine against metastatic breast cancer reveals a dual mode of action. *Cancer Res.* 69, 5860-5866 (2009).
12. E. Muraille, E. Narni-Mancinelli, P. Gounon, D. Bassand, N. Glaichenhaus, L. L. Lenz, G. Lauvau, Cytosolyc expression of SecA2 is a prerequisite for long-term protective immunity. *Cell. Microbiol.* Doi: 10.111/j. 1462-5822.2007.00883.x (2007).
13. Targeted Radionuclide Therapy. Ed. Tod Speer, Lippincott, Williams & Wilkins, Philadelphia (2010).
14. L. Bodel, M. Cremonesi, C. Grana, P. Rocca, M. Bartelomei, M. Chinol, G. and Paganelli, Receptor radionuclide therapy with 90Y-[DOTA]0-Tyr3-octreotide (90YDOTATOC) in neuroendocrine tumors. *Eur. J. Med. And Mol. Imaging.* 31, 1038-1046, 2004.
15. D. E. Milenic, K. Garmestani, E. D. Brady, P. S. Albert, D. Ma, A. Abdulla, M. W. Brechbiel, Alpha-particle radioimmunotherapy of disseminated peritoneal disease using a (212)Pb-labeled radio-immunoconjugate targeting HER2. *Cancer Biother Radiopharm,* 20, 557-68 (2005).
16. D. V. Gold, Z. Karanjawala, D. E. Modrak, D. M. Goldenberg, R. H. Hruban, PAM4-reactive MUC1 is a biomarker for early pancreatic adenocarcinoma. *Clin. Cancer Res.* 13, 7380-7 (2007).
17. A. Sultana, S. Shore, M. G. Raraty, S. Vinjamuri, J. E. Evans, C. T. Smith, S. Lane, S. Chauhan, L. Bosonnet, C. Garvey, R. Sutton, J. P. Neoptolemos, P. Ghaneh, Randomised Phase I/II trial assessing the safety and efficacy of radiolabelled anticarcinoembryonic antigen I(131) KAb201 antibodies given intra-arterially or intravenously in patients with unresectable pancreatic adenocarcinoma. *BMC Cancer* 25, 966-971 (2009).
18. E. Dadachova, J. D. Nosanchuk, L. Shi, A. D. Schweitzer, A. Frenkel, J. S. Nosanchuk, and A. Casadevall. Dead cells in melanoma tumors provide abundant antigen for targeted delivery of ionizing radiation by a monoclonal antibody to melanin. *Proc. Natl. Acad. Sci. USA,* 101, 14865-14870 (2004).
19. S. H. Kim, F. Castro, D. Gonzalez, P. C. Maciag, Y. Paterson, C. Gravekamp, Mage-b vaccine delivered by recombinant *Listeria monocytogenes* is highly effective against breast cancer metastases. *B.J.C.* 99, 741-49 (2008).
20. P. C. Maciag, S. Radulovic, J. Rothman, The first clinical use of a live-attenuated *Listeria monocytogenes* vaccine: A Phase I safety study of LM-LLO-E7 in patients with advanced carcinoma of the cervix. *Vaccine* 27, 3975-3983 (2009).
21. C. Gravekamp, and Y. Paterson, Harnessing *Listeria monocytogenes* to target tumors. *Cancer Biol. and Ther.* 9, 1-9 (2010).
22. M. Lotem, T. Peretz, Mizrachi, Y. Liberman, E. Dadachova, A. Casadevall, A. de Kater, N. Friedmann, G. B. Thornton, M. Klein. Two Phase I studies of PTI-188, a radiolabeled murine antimelainin antibody, in patients with metastatic melanoma (MM). *J Clin Oncol* 29, 2011 (suppl: abstract 8555).
23. Y. A. Yu, S. Shabahang, T. M. Timiryasova, Q. Zhang, R. Beltz, I. Gentschev, W. Goeble, A. A. Szalay, Visualization of tumors and metastases in live animals with bacteria and vaccinia virus encoding light-emitting proteins. *Nature Biotechnology* 22, 313-320 (2003).
24. S. Patyar, R. Joshi, D. S. P. Byrav, A. Prakash, B. Medhi, B. K. Das, Bacteria in cancer therapy: a novel experimental strategy. J. Biomed. Sci. 17, 21 (2010). (worldwideweb.jbiomedsci.com/content/17/1/21).
25. S. Demaria, N. Bhardwaj, W. H. McBride, and S. C Formenti, Combining radiotherapy and immunotherapy: a revived partnership. *Int. J. Radial. Oncol. Biol. Phys.* 63, 655-666 (2005).
26. E. J. Friedman, Immune modulation by ionizing radiation and its implications for cancer immunotherapy. *Curr. Pharm. Des.* 8, 1765-1780 (2002).
27. J. W. Conlan, Early pathogenesis of *Listeria monocytogenes* infection in the mouse spleen. *J. Med. Microbiol.* 44, 295-302 (1996).
28. P. Racz, K. Tenner, and E. Mero, Experimental Listeria enteritis. I An electron microscopic study of the epithelial phase in experimental listeria infection. *Lab Invest* 26, 694-700 (1972).
29. H. Rosen, And S. Gordon. Monoclonal antibody to murine type 3 complement receptor inhibits adhesion of myelomonocytic cells in vitro and inflammatory cell recruitment in vivo. *J. Exp. Med.* 166, 1685-1701 (1987).
30. G. R. Gunn, A. Zubair, C. Peters, Z. K. Pan, T. C. Wu, and Y. Paterson, Two *Listeria monocytogenes* vaccine vectors that express different molecular forms of human papillomavirus-16 (HPV-16) E7 induce qualitatively different T cell immunity that correlates with their ability to induce regression of established tumors immortalized by HPV-16. *J. Immunol.* 167, 6471-6479 (2001).
31. R. Singh, M. E. Domineicki, E. M Jaffee, and Y. Paterson, Fusion of Listeriolysin O and delivery by *Listeria monocytogenes* enhances the immunogenicity of HER-2/neu and reveals subdominant epitopes in the FVB/N mouse. *J. Immunol.* 175, 3663-3673 (2005).
32. R. Sypniewska, L. Hoflack, M. Tarango, S. Gauntt. R. Reddick, and C. Gravekamp, Prevention of metastases with a Mage-b DNA vaccine in a mouse breast tumor model: potential for breast cancer therapy. *B.C.R.T.* 91, 19-28 (2005).
33. F. Castro, B. Leal, A. Denny, R. Bahar, S. Lampkin, R. Reddick, S. Lu, C. Gravekamp, Vaccination with Mage-b DNA induces CD8 T cell responses at young but not at old age in mice with metastatic breast cancer. *B.J.C.* 101, 1329-1337 (2009).

What is claimed is:

1. A method of treating metastases of a prostate tumor in a subject, comprising administering to the subject an amount of attenuated *Listeria monocytogenes* labelled or loaded with $^{32}$P or $^{188}$Re (radiolisteria) effective to selectively accumulate the radiolisteria in the metastases of the prostate tumor as compared to in the prostate tumor, so as to treat the metastases of the prostrate tumor in the subject, wherein the radiolisteria is administered to the subject once a day for at least seven days.

2. The method claim 1, wherein the attenuated *Listeria monocytogenes* is genetically modified.

3. The method of claim 1, wherein the radiolisteria is labelled or loaded with $^{188}$Re.

4. The method of claim 1, wherein the radiolisteria comprises $^{32}$P by means of having been cultured in a radionuclide-containing medium.

5. The method of claim 1, wherein radiolisteria is labelled with $^{32}$P or $^{188}$Re, and the $^{32}$P or $^{188}$Re is bound to an antibody attached to the attenuated *Listeria monocytogenes*.

6. The method of claim 1, wherein radiolisteria comprises $^{188}$Re by means of having been cultured in a radionuclide-containing medium.

7. The method of claim 1, wherein the radiolisteria are administered systemically to the subject.

8. The method of claim 1, wherein the prostate tumor is an inoperable tumor.

9. A method of treating metastases of a pancreatic tumor in a subject, comprising administering to the subject an amount of attenuated *Listeria monocytogenes* labelled or loaded with $^{32}$P or $^{188}$Re (radiolisteria) effective to selectively accumulate the radiolisteria in the metastases of the pancreatic tumor as compared to in the pancreatic tumor, so as to treat the metastases of the pancreatic tumor in the subject, wherein the radiolisteria is administered to the subject once a day for at least seven days.

* * * * *